United States Patent [19]

Sucov et al.

[11] Patent Number: 5,091,518
[45] Date of Patent: Feb. 25, 1992

[54] BETA RETINOIC ACID RESPONSE ELEMENTS COMPOSITIONS AND ASSAYS

[75] Inventors: Henry M. Sucov, San Diego; Ronald M. Evans, La Jolla, both of Calif.

[73] Assignee: The Salk Institute for Biological Studies, San Diego, Calif.

[21] Appl. No.: 438,757

[22] Filed: Nov. 16, 1989

[51] Int. Cl.$^5$ .............................................. C07H 17/00
[52] U.S. Cl. ................................. 536/27; 435/172.3; 435/320.1; 536/28; 536/29; 935/6; 935/9; 935/22; 935/33
[58] Field of Search ...................... 435/172.3, 320.1; 536/27, 28, 29; 935/6, 9, 22, 33

[56] References Cited

PUBLICATIONS

Chandler et al., Cell, vol. 33, 489–499, Jun. 1983.
Klein-Hitpass Nucleic Acids Research, vol. 16, No. 2 647–663 (1988).
Evans, Science, vol. 240 889–895, May 13, 1988.
Green et al., Trends in Genet., Nov. 1988, vol. 4, No. 11, 309–314.
Umesono et al., CA Abstracts: CA110 (3): 19312q, Nature (London), 336(6196) 262–265 (1988).

*Primary Examiner*—Amelia Burgess Yarbrough
*Assistant Examiner*—Lori L. Yuan
*Attorney, Agent, or Firm*—Pretty, Schroeder, Brueggemann & Clark

[57] ABSTRACT

The present invention provide transcriptional control regions, expression vectors comprising said regions, mammalian cells transformed to transcribe and express genes from said vectors, and various methods of assaying compounds for hormone agonist or antagonist activity, all based on discovery of response elements of the $\beta$-retinoic acid receptor and of the activation of said response elements in all mammalian cells without need to transform the cells to express the receptor independently of endogenous expression thereof.

14 Claims, 3 Drawing Sheets

FIG. 1-1

```
SacII
CCGCGGCGCT  GGCTGAAGGC  TCTTGCAGGG  CTGCTGGGAG  TTTTTAAGCG  CTGTGAGAAT   60
                                                            SmaI
CCTGGGAGTT  GGTGATGTCA  GACTGGTTGG  GTCATTTGAA  GGTTAGCAGC  CCGGGAAGGG  120
TTCACCGAAA  GTTCACTCGC  ATATATTAGG  CAATTCAATC  TTTCATTCCG  TGTGACAGAA  180
            SacII
GTGGTAGGAA  GTGAGCTGCT  CCGAGGCAGG  AGGGTCTATT  CTTTGCCAAA  GGGGGGACC   240
                                                            SmaI
AGAGTTCCCG  TGCGCCGCGG  CCACAAGACT  GGGATGCAGA  GGACGCGAGC  CACCCGGGCA  300
GGGAGCGTCT  GGGCACCGGC  GGGTAGGAC   CCGCCGCTC   CCGGAGCCTG  CGCGGGCGTC  360
GCCTGGAAGG  GAGAACTTGG  GATCGGTGCG  GGAACCCCCG  CCCTGGCTGG  ATCGGCCGAG  420
CGAGCCTGGA  AAATGGTAAA  TGATCATTTG  GATCAATTAC  AGGCTTTTAG  CTGGCTTGTC  480
TGTCATAATT  CATGATTCGG  GGCTGGGAAA  AAGACCAACA  GCCTACGTGC  CAAAAAGGG   540
```

```
                                                                                        600
GCAGAGTTTG ATGGAGTTCG TGGACTTTTC TGTGCGGCTC GCCTCCACAC CTAGAGGATA

653
AGCACTTTTG CAGAGCGCGG TGCGGAGAGA TC ATG TTT GAC TGT ATG GAT GTT
                                        Met Phe Asp Cys Met Asp Val
                                         1               5

701
CTG TCA GTG CCC GGG CAG ATC CTG GAT TTC TAC ACC GCG AGC CCT
Leu Ser Val Ser Pro Gly Gln Ile Leu Asp Phe Tyr Thr Ala Ser Pro
         10                      15                      20

749
TCC TCC TGC ATG CTG CAG GAA AAG GCT CTC AAA GCC TGC CTC AGT GGA
Ser Ser Cys Met Leu Gln Glu Lys Ala Leu Lys Ala Cys Leu Ser Gly
     25                      30                      35

798
TTC ACC CAG GCC GAA TGG CAG CAC CGG CAT ACT GCT CAA TGTAGGTTTA
Phe Thr Gln Ala Glu Trp Gln His Arg His Thr Ala Gln    ↓SPLICE DONAR
         40                      45                 50      SITE

858
TTTTTTTTT TCCTTTCTTT TACCAAGGAA AAATAAATGT CTCTCTTGCA TGCAATAAAG

900
ACACTGGAAT AAAGTGCAGT GGTGGCAAGA CAAAGGGTTT AA

FIG. 1-2
```

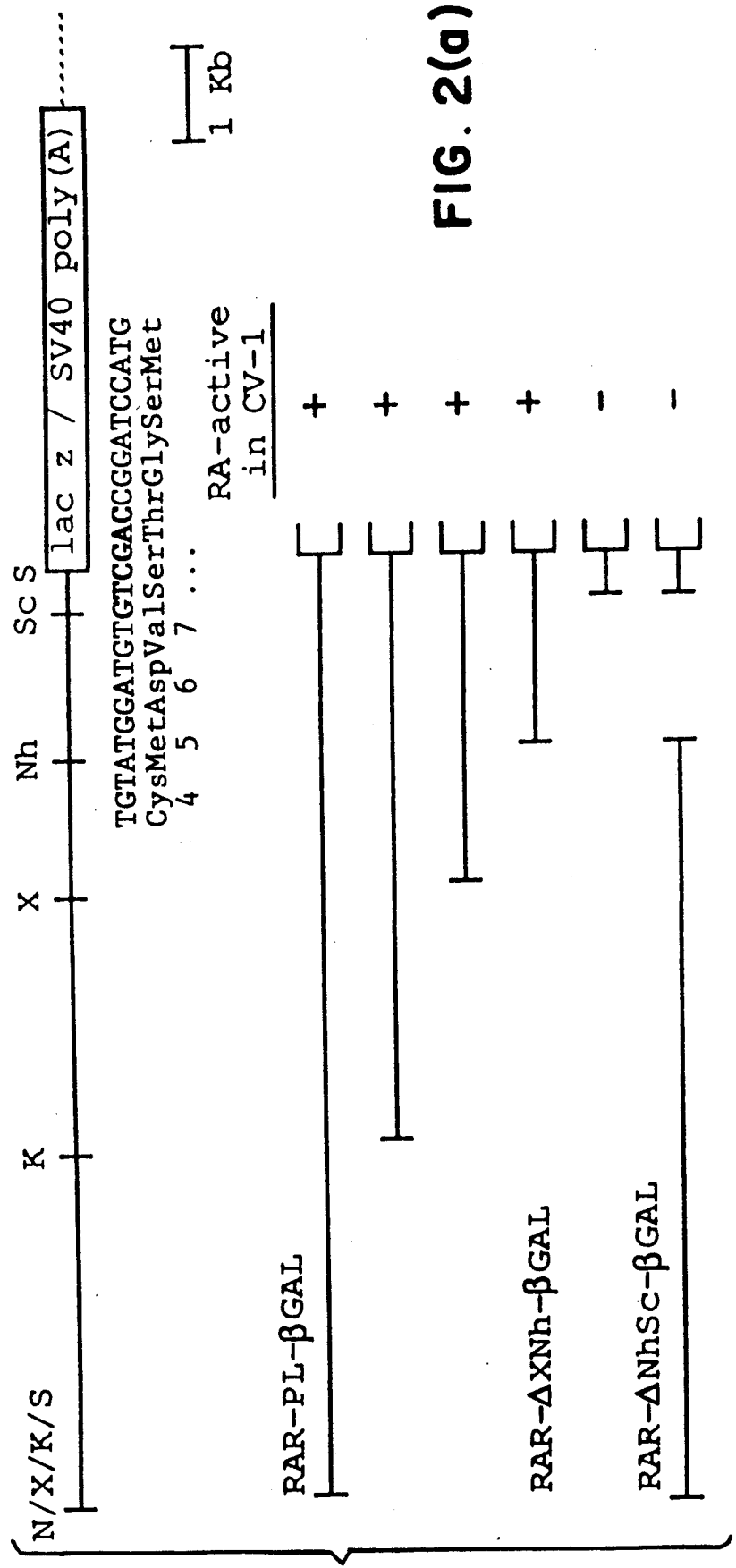

BETA RETINOIC ACID RESPONSE ELEMENTS COMPOSITIONS AND ASSAYS

The invention described and claimed herein was made with support from the United States National Institutes of Health. The United States Government has certain rights in the invention.

FIELD OF THE INVENTION

The present invention relates generally to the superfamily of nuclear receptors known as the steroid/thyroid hormone receptors and their cognate response elements. More particularly, the present invention relates to discovery of β-retinoic acid response elements (βRARES), which may be used to enhance transcriptional activity of promoters.

BACKGROUND OF THE INVENTION

A central question in eukaryotic molecular biology is how specific DNA-binding proteins bind regulatory sequences to influence cell function and fate. The steroid/thyroid hormone receptors form a superfamily of ligand-dependent transcription factors that are believed to play a part in such cell function and fate. For example, it is known that these receptors transduce extracellular hormonal signal to target genes that contain specific enhancer sequences referred to as hormone-response elements (HREs). Each receptor contains a ligand-binding domain and a DNA-binding domain. The receptor undergoes a conformational change when it binds ligand which conformational change permits the receptor-ligand complex to bind its cognate response element and thereby regulate transcriptional activity of an associated promoter, which drives transcription of an operatively associated structural gene.

Sequence comparison and mutational analyses of hormone receptors such as glucocorticoid receptor (GR) have identified functional domains responsible for transcriptional activation and repression, nuclear localization, DNA binding, and hormone binding. The DNA binding domain, which is required in order to activate transcription, consists of 66-68 amino acids of which about 20 sites, including nine cysteines ($C_1$ to $C_9$), are invariant among different receptors. The modular structure of members of this receptor superfamily allows the exchange of one domain for another to create functional, chimeric receptors.

The hormone response elements are generally structurally related but in fact are functionally distinct. Those for GR (GRE), estrogen receptor (ERE), and thyroid hormone receptor response elements (TRE) have been characterized in detail; they consist of a palindromic pair of 'half sites' (Evans, Science 240, 889 (1988); Green and Chambon, Trends In Genetics 4, 309 (1988)). With optimized pseudo- or consensus response elements, only two nucleotides per half site are different in GRE and ERE (Klock, et al., Nature 329, 734 (1987)). On the other hand, identical half sites can be seen in ERE and TRE, but their spacing is different (Glass, et al., Cell 54, 313 (1988)). Moreover, TRE has been shown to mediate transcriptional activation by transfected retinoic acid receptors (RARs) in CV-1 cells whereas non-transfected cells show no response. (Umesono et al., Nature 336, 262 (1988)). In other words, both TR and RR receptors can activate TREs.

It is, thus, surprising that the β-retinoic acid response elements (βRAREs) disclosed herein have a tandem repeat sequence as opposed to a palindromic sequence, and are much less susceptible to transcriptional activation by non-cognate receptors (e.g., estrogen receptor (ER), GR, thyroid hormone receptor (TR), etc.) than the known response elements (GRE, ERE, TRE). Also surprising is that constructs having βRAREs in a wide variety of mammalian cells have shown robust retinoic acid (RA)-dependent induction in the absence of cotransfected retinoic acid receptor (RAR)-encoding expression vector. This discovery suggests that virtually all mammalian cells express a low level of endogenous βRAR that is sufficient for efficient activation of vectors containing the βRARE, but apparently below a threshold for activation of the previously studied TREs.

Thus, using transcriptional control regions comprising βRARE and a functional promoter, it is now possible to provide recombinant DNA vectors containing a gene, the transcription (and, thereby, also expression) of which is under the control of a promoter, the transcriptional activity of which is responsive to (and increased by) retinoic acid, without the necessity of cotransfection with a vector providing expression of RAR.

SUMMARY OF THE INVENTION

We have discovered, and characterized by sequence, DNA segments which are βRAREs and linkages, between said segments and promoters, which are operative to confer responsiveness to retinoic acid on transcriptional activities of the promoters in mammalian cells. We have also discovered that the transcriptional activity enhancing effect of βRAREs occurs in all mammalian cells in the presence of retinoic acid, indicating that βRAR is present endogenously in all of these cells.

DETAILED DESCRIPTION OF THE INVENTION

In the present specification and claims, reference will be made to phrases and terms of art which are expressly defined for use herein as follows:

As used herein, RARβ or βRAR means retinoic acid receptor beta.

As used herein, CAT means chloramphenicol acetyltransferease; LUC mean firefly luciferase; β-Gal means βgalactosidase.

As used herein, COS means monkey kidney cells which express T antigen (Tag). See Gluzman, Cell, 23:175 (1981).

As used herein, CV-1 means mouse kidney cells from the cell line transferred to as "CV-1". CV-1 is the parental line of COS. Unlike COS cells, which have been transformed to express SV40 T antigen (Tag), CV-1 cells do not express T antigen.

As used herein, βRARE's mean β retinoic acid response elements βRARE's are enhancer-like DNA sequences that confer retinoic acid (RA) responsiveness via interaction with the βRAR-RA complex, to transcriptional activity of promoters linked operatively for such responsiveness to a βRARE.

As used herein, the terms "transcriptional control region" or "transcriptional control element", means a DNA segment comprising a βRARE operatively linked to a promoter to confer retinoic acid responsiveness to transcriptional activity of the promoter.

As used herein, in the phrase "operatively linked" means that the linkage (i.e., DNA segment) between the DNA segments so linked is such that the described effect of one of the linked segments on the other is capable of occuring.

Effecting operable linkages for the various purposes stated herein is well within the skill of those of ordinary skill in the art, particularly with the teaching of the instant specification.

As used herein, the phrase "promoter being naturally unresponsive to RA" means that RA does not enhance transcription from the promoter to an observable extent in a mammalian cell unless a βRARE is spliced or inserted, by recombinant DNA or genetic engineering methods, into a DNA segment comprising the promoter upstream of the promoter (relative to the direction of transcription therefrom) and linked to the promoter in a manner which makes operative responsiveness to RA of the transcriptional activity from the promoter.

Use of the term "substantial sequence homology" in the present specification and claims means it is intended that DNA or RNA sequences which have de minimus sequence variations from, and retain the same functions as, the actual sequences disclosed and claimed herein are within the scope of the appended claims.

The nucleotides which occur in the various nucleotide sequences appearing herein have their usual single-letter designations (A, G, T, C or U) used routinely in the art.

In the textual portion of the present specification and claims, references to Greek letters may be written as alpha, beta, etc. In the Figures and elsewhere in the specification, the corresponding Greek letter symbols are sometimes used.

In one of its aspects, the invention is a vector for expression in a mammalian cell of a protein, said expression under control of a transcriptional control region of the vector, said transcriptional control region comprising (1) a promoter, which is linked operatively for transcription to a first DNA segment, which is expressed as the protein, and (2) a second DNA segment, which comprises a subsegment of sequence 5'-GTTCAC$n_1n_2n_3n_4n_5$GTTCAC-3', wherein $n_1$, $n_2$, $n_3$, $n_4$ and $n_5$ are independently A, T, C or G, said subsegment of said second DNA segment being linked operatively to said promoter to confer responsiveness to retinoic acid on transcriptional activity from the promoter, provided that the transcriptional activity of the promoter is naturally unresponsive to retinoic acid.

With respect to the promoter which is part of a transcriptional control region of the invention, practically any promoter may be used, so long as the transcriptional activity of such a promoter may be enhanced by a βRARE-containing DNA segment suitably positioned upstream from the promoter and provided that such promoter is naturally unresponsive, in its transcriptional activity, to retinoic acid. Among such promoters are Delta-MTV promoter, Herpes thymidine kinase (tk) promoter and basal SV-40 promoter. Very desirable are promoters which require a response element for activity. On the other hand, very strong promoters, which drive transcription in the absence of enhancers, are not desirable promoters for use in the transcription control regions, and vectors, of the invention.

Virtually any protein or polypeptide of interest can be made with mammalian cell transformed with an expression vector of the invention. Such proteins include hormones, lymphokines, receptors or receptor subunits, immunoglobulin chains and the like. Indicator proteins such as LUC, CAT and β-Gal can also be made.

In another of its aspects, the invention entails a mammalian cell transformed to express a protein from a vector for expression of said protein, said vector comprising a transcriptional control region comprising (1) a promoter, which is linked operatively for transcription to a first DNA segment, which is expressed as the protein, and (2) a second DNA segment, which comprises a subsegment of sequence 5'-GTTCAC$n_1n_2n_3n_4n_5$GTTCAC-3', wherein $n_1$, $n_2$, $n_3$, $n_4$ and $n_5$ are independently A, T, C or G, said subsegment of said second DNA segment being linked operatively to said promoter to confer responsiveness to retinoic acid on transcriptional activity from the promoter, provided that the transcriptional activity of the promoter is naturally unresponsive to retinoic acid.

Among the types of mammalian cells that can be transformed in accordance with the invention are CV-1, COS, F9, P19, CHO, HeLa, NIH 3T3, Rat2 fibroblast, HT1080.T, chick embryo fibroblasts and quail QT6 cells.

In still another aspect, the invention entails method for testing activity of a test compound as an agonist or antagonist of retinoic acid, said method comprising:

(a) culturing (i) in the presence of retinoic acid and the absence of test compound and (ii) in the presence of both retinoic acid and test compound, a mammalian cell transform to express a protein from a vector for expression of said protein, said vector comprising a transcriptional control region comprising (1) a promoter, which is linked operatively for transcription to a first DNA segment, which is expressed as the protein, and (2) a second DNA segment, which comprises a subsegment of sequence 5'-GTTCAC$n_1n_2n_3n_4n_5$GTTCAC-3', wherein $n_1$, $n_2$, $n_3$, $n_4$ and $n_5$ are independently A, T, C or G, said subsegment of said second DNA segment being linked operatively to said promoter to confer responsiveness to retinoic acid on transcriptional activity from the promoter, provided that the transcriptional activity of the promoter is naturally unresponsive to retinoic acid; and (b) comparing the amount of said protein expressed during the two culturing of step (a).

The cells of the invention, including those employed in the method of testing compounds for RA activity, can optionally be co-transformed with an expression vector which expresses βRAR.

Indeed, because a low level of responsiveness of βRAREs (in enhancing transcription from an operatively linked promoter) has also been observed with TR's and vitamin D3 receptor (VD3R), agonists and antagonists of thyroid hormones and vitamin D3 can be screened for by testing compounds, as described above, but using cells transfected with a suitable vector of the present invention and a vector expressing TR or VD3R.

Receptors, assay methods, and other subject matter pertinent to the subject matter of the present specification may be found in the following references, which are incorporated herein by reference: Commonly assigned U.S. patent application Ser. No. 108,471, filed Oct. 20, 1987 and published as PCT International Publication No. WO 88/03168; commonly assigned U.S. patent application Ser. No. 276,536, filed Nov. 30, 1988 and published as European Patent Application Publication No. 0 325 849; commonly assigned U.S. patent application Ser. No. 370,407, filed June 22, 1989, said Application listing a Budapest Treaty Deposit of a plasmid harboring a cDNA encoding a gamma-retinoic acid receptor, said deposit having been made June 22, 1989 and bearing American Type Culture Collection Accession No. 40623; Zelent et al., Nature 339, 714 (1989); Petkovich et al., Nature 330, 444 (1987); Brand et al., Nature 332, 850 (1988).

In another of its aspects, the present invention entails a DNA segment for controlling transcription of a gene in a mammalian cell, said segment comprising a promoter linked operatively for transcription to the gene and a subsegment with the sequence 5'-GTTCACn$_1$n$_2$n$_3$n$_4$n$_5$GTTCAC-3', wherein n$_1$, n$_2$, n$_3$, n$_4$ and n$_5$ are independently A, T, G or C, said subsegment linked operatively to said promoter to confer responsiveness to retinoic acid on transcriptional activity from the promoter, provided that transcriptional activity from the promoter is naturally unresponsive to retinoic acid.

βRARE may be provided on a DNA segment which possesses a tandem repeat of the 6 bp motif 5'-GTTCAC separated by 5 bp sequence, which sequence may be any randomly chosen nucleotide sequence. Especially preferred βRAREs are provided on the segments

5'-AAGCTTAAGGGTTCACCGAAAGTTCACTCAGCTT,

5'-AAGCTTAAGGGTTCACCGAAAGTTCACTCGCATAGCTT and

5'-AAGCTTAAGGGTTCACCGAAAGTTCACTCGCATATATTAGCTT, which DNA segments are adapted at the 5'- and 3'- ends to include a convenient restriction endonuclease site.

Because the DNA segments which comprise the βRARE are relatively short, they may be provided synthetically, that is by synthesizing the βRARE-containing oligonucleotide on a DNA synthesizer as is known in the art. It is very desirable to provide restriction endonuclease sites at the 3' and 5' end of the oligomer, such that the synthetic βRARE may be conveniently inserted into a DNA expression vector at a site upstream from the promoter, whose transcriptional activity is to be enhanced and which driving transcription of the desired gene. As those of ordinary skill in the art will understand, βRAREs, like other response elements, and orientation and, with wide latitude, position independent. Thus, βBRARE is functional in either orientation and may be placed in any convenient location from about 30 nucleotides upstream to about 10,000 nucleotides upstream from the promoter to be affected.

Preferred mammalian cells for use with the enhanced expression systems of the invention employing transcriptional control regions comprising beta-retinoic acid response element are COS cells and CV-1 cells. COS-1 (referred to as COS) cells are mouse kidney cells that express SV40 T antigen (Tag); CV-1 do not express SV40 Tag. CV-1 cells are convenient because they lack any endogenous glucocorticoid or mineralocorticoid or other known steroid or thyroid hormone receptors, except that they do produce low levels of βRAR. Thus, via gene transfer with appropriate expression vectors comprising a heterologous gene under the control of a transcriptional control region of the invention, it is possible to convert these host cells into transformed cells which produce increased quantities of a desired protein in response to induction by retinoic acid.

Expression plasmids containing the SV40 origin of replication, can propagate to high copy number in any host cell which expresses SV40 Tag. Thus, expression plasmids carrying the SV40 origin of replication can replicate in COS cells, but not in CV-1 cells. Although increased expression afforded by high copy number is desirable, it is not critical to the disclosed assay system. The use of any particular cell line as a host is also not critical, although CV-1 cells are preferred because they are particularly convenient for gene transfer studies and provide a sensitive and well described host cell system.

EXAMPLE

The following demonstrates that the sequences in the promoter of the mouse RARb gene confer RA responsiveness, and that these sequences represent a target specific for the three RA receptor subclasses (alpha-, beta- and gamma-RAR). The RA response element (RARE) does not mediate significant transcriptional activation by estrogen, glucocorticoid, but does weakly (about one order of magnitude less) mediate transcriptional activatin by vitamin D or thyroid hormone receptors (complexed with cognate ligands)

A mouse liver genomic DNA library (Clonetech) in lambda vector EMBL3 was screened with a human RARb cDNA probe to localize the RARE in the RARb gene. This resulted in the isolation of a genomic fragment containing approximately 10 kb of upstream sequence, the complete first exon, and 10 kb of the first intron. The sequence of a portion of this clone containing the first exon and proximal 5' DNA is shown in FIG. 1. The 10 kb upstream region was fused in-frame just downstream of the RARb translation initiation codon to a b-galactosidase reporter gene (FIG. 2a). RAR-PL-bGAL was introduced into monkey kidney CV-1 cells cotransfected with RAR expression vector. Enzyme activity was induced upon retinoic acid addition, indicating that this region of genomic DNA contains a functional promoter which is responsive to retinoic acid. This was accomplished by introducing a SalI restriction site was introduced into the genomic clone at the indicated position by site-directed mutagenesis; the 10 kb genomic fragment was then excised and cloned into the b-galactosidase vector pLSV (a derivative of pGH101 (Herman, G. E., O'Brien, W. E. and Beaudet, A. L. Nucl. Acids Res., 14, 7130 (1986), modified to contain a SalI site and a polylinker sequence by oligo addition, to yield RAR-PL-bGAL.

A series of deletions from the 5' end of RAR-PL-bGAL reveal that sequences mediating RA induction reside within the 2 kb NheI-SacII fragment (FIG. 2a; Table below). Subfragments of this region were cloned into the enhancer-dependent luciferase reporter plasmid DMTV-LUC, which contains the mouse mammary tumor virus promoter with the natural GR response elements deleted (Hollenberg, S. M. and Evans, R. M. Cell, 55, 899–906 (1988)). A 183 bp SmaI fragment (see FIG. 1) is able to confer retinoic acid responsiveness to this heterologous promoter in either orientation (Table). Oligonucleotide sequences (FIG. 2b) derived from this region were then used to further define the RA response element, either in DMTV-LUC or DMTV-CAT (Table below).

Thyroid hormone response element (TRE) has been shown to mediate transcriptional activation by transfected RARs in CV-1 cells, whereas non-transfected cells show no response. Umesono et al, Nature 336, 262–265 (1988). Surprisingly, when Delta-MTV-CAT constructs βRE1, βRE2, and βRE3 (FIG. 2) showed robust RA-dependent induction in the absence of co-transfected RAR expression vector. Cotransfection of RAR-alpha expression vector increased induction by only two-fold, which demonstrates that CV-1 cells express a low level of endogenous RA receptor that is sufficient for efficient activation of vectors containing the βRE, but apparently below a threshold for activation of the previously studied TREs. A survey of the following cell lines indicated that all were able to efficiently transactivate the βRARE in an RA-dependent fashion in the absence of transfected RAR expression vector: CV-1, F9 and P19 (mouse teratocarcinomas), CHO, HeLa, NIH 3T3, Rat2 fibroblasts, HT1080.T (human lymphoid), chick embryo fibroblasts, and quail QT6 cells. No cell line has yet been tested which does not express this activity. vector.

Inspection of the sequences of βRE1, βRE2 and βRE3 (FIG. 2b) identifies a tandem repeat of the 6 bp motif GTTCAC. The center to center separation of 11 bp between these repeats is one turn of the DNA helix. Constructs containing single copies of either the 5' or 3' half site (βRE4 and βRE5) are functional only upon cotransfection of RAR expression vectors (FIG. 2d). Not only does this indicate that the RARE is a bonafide target of all three RAR subtypes expressed from cloned cDNA, but also demonstrates that these half sites can serve as a minimal RA response element in the context of the Delta-MTV promoter. Apparently a single half-site (5'-GTTCAC-3') is a low affinity target requiring high levels of receptor for activation, and that the two sequences, when juxtaposed as a tandem repeat, create a high affinity binding site (via cooperative interactions) which is able to respond to the low level of endogenous RAR present in CV-1 and other cells.

To demonstrate that the sequences described above are direct binding sites for the RAR, extracts from transfected cells were mixed with $^{32}P$-labeled RARE, and the resulting complex immunoprecipitated with antibody specific to the transfected receptor For this purpose, a hybrid receptor (termed GRR) was created in which the amino terminus of the glucocorticoid receptor was coupled to the DNA binding and ligand binding domains of RARa. This hybrid receptor exhibits the RA dependence and target gene specificity of the RAR. (D. Mangelsdorf et al. unpublished observations). COS cell extracts containing the hybrid receptor specifically immunoprecipitate labeled βRE2 oligo. Binding of GRR to βRE2 in this assay is not affected by the addition of an excess of unlabeled GRE competitor, but is competed by an excess of either the β-response element itself or a TRE sequence, another known RAR binding site. In a parallel set of experiments, GR extract specifically binds to labeled GRE, is competed by excess unlabeled GRE, and does not recognize the βRE2 sequence. Thus, specific binding to the β-response element is observed by the hybrid GRR receptor.

Many previously characterized response elements are targets of more than one type of receptor: both the RAR and the TR are able to activate a TRE; the RAR, TR, and estrogen receptor all activate the vitellogenin ERE; the progesterone, mineralocorticoid, and GR all activate the GRE (Ham et al., Nucl. Acids Res. 16, 5263-5276 (1988)). Thus, it might be expected that the response element of the RARb gene would reciprocally be responsive to the TR, ER, and/or other members of the receptor superfamily. Cotransfection of the ER, GR, in CV-1 cells with construct βRE1 failed to result in appreciable activation in the absence or following addition of the appropriate ligand, although cotransfection with TR and vitamin D receptor (VD3R) CV-1 cells with construct βRE1 did weakly (about 10- to 20-fold less) activate their cognate response elements.

5 ug of each of the constructs indicated in the Table below were transfected into CV-1 cells with either RSV-LUC or RSV-bGAL to normalize transfection efficiencies. Transfections also included RARa expression vector. Each value represents duplicate measurements of plates treated with $10^{-7}M$ RA (βGAL experiments) or $10^{-6}M$ RA (luciferase experiments) relative to plates treated with solvent only. The 183 bp SmaI restriction fragment (shown in FIG. 1) was inserted either in the forward (F) or reverse (R) orientation relative to the Delta-MTV promoter. The (NR) construct contains a 45 bp oligo sequence located 24 bp 3' of bRE1 in the RARb promoter which was nonresponsive to RA.

Plasmids were transfected into CV-1 cells and assayed for β-galactosidase activity either without or with the addition of $10^{-7}M$ RA. Negative responses were two-fold induction or less; positive inductions were seven-fold or greater.

Cells were transfected in 10 cm dishes with 10 ug DNA containing 5 ug reporter plasmid, 1-2 ug either RSV-LUC (a), or RSV-bGAL or pCH110 (c and d), pGEM4 as carrier DNA, and for the experiments shown in a and d, 1 ug RSV-RAR expression vector or the same amount of an RSV vector generating a non-sense transcript. Cells were harvested 1 day after addition of retinoic acid. All CAT assays represent equivalent amounts of b-galactosidase activity; bGAL assays were normalized to luciferase activity.

| Retinoic acid inducibility of reporter constructs | |
|---|---|
| Construct | Fold increase |
| RAR-PL-bGAL | 14 |
| RAR-DXN-bGAL | 22 |
| RAR-DNhSc-bGAL | 2 |
| DMTV-LUC | 2 |
| DMTV-Smal83F-LUC | 10 |
| DMTV-Smal83R-LUC | 9 |
| DMTV-LUC | 2 |
| DMTV-(NR)-LUC | 2 |
| DMTV-bRE1-LUC | 14 |

DESCRIPTION OF THE DRAWINGS

FIG. 1 represents the sequence of the mouse βRAR promoter region and first exon. The TATA and GTTCAC motifs are underlined; the first exon splice site is indicated with an arrow. A mouse liver genomic DNA library (Clonetech) in the lambda vector EMBL3 was screened with the BamHI-SphI fragment of the human RARb cDNA clone B1-RARe. See, Benbrook et al, Nature 333, 669-672 (1988). This probe contains only first exon sequences, which are unique to the βRAR gene. A clone harboring a 20 kb insert was isolated, and the region surrounding the first exon subcloned and subjected to dideoxy sequence analysis.

FIG. 2(a) represents the in vivo analysis of RARβ RA response element sequences, following a series of deletions from the 5' end of the sequence including the β retinoic acid response element. The sequence at the junction between the mouse RARβ gene and the β-galactosidase reporter gene is as shown. Numbered amino acids correspond to the native RARβ translation product. Restriction sites are N, NotI; X, XhoI; K, KpnI; S, SalI; Nh, NheI; Sc, SacII. The dotted line represents plasmid sequences.

FIG. 2(b) represents sequences of oligonucleotides including the β retinoic acid response element used in these experiments. The terminal lower case bases are foreign to the RARβ promoter, and were included to allow insertion into the unique HindIII site of the Delta-MTV vector.

We claim:

1. A substantially pure DNA having the sequence:

5'-GTTCAC-$n_1n_2n_3n_4n_5$-GTTCAC-3', wherein $n_1$, $n_2$, $n_3$, $n_4$, and $n_5$ are each independently selected from A, T, C, or G.

2. A DNA according to claim 1 wherein $n_1$ is C, $n_2$ is G, $n_3$ is A, $n_4$ is A, and $n_5$ is A.

3. A DNA according to claim 2 having the sequence:

5'-AAGCTTAAGG-GTTCAC-CGAAA-GTTCAC-TCAGCTT-3'.

4. A DNA according to claim 3 having the sequence:

5'-AAGCTTAAGG-GTTCAC-CGAAA-GTTCAC-TC-GCAT-AGCTT-3'.

5. A DNA according to claim 4 having the sequence:

5'-AAGCTTAAGG-GTTCAC-CGAAA-GTTCAC-TCGCAT-ATATT-AGCTT-3'.

6. A substantially pure DNA construct comprising the DNA of claim 1 operatively linked to a promoter which is not normally subject to transcriptional activation by retinoic acid; wherein the DNA and the promoter are operatively linked so as to confer transcriptional activation activity on said promoter in the presence of retinoic acid.

7. A substantially pure DNA construct comprising a DNA segment selected from:

5'-GTTCAC-CGAAA-GTTCAC-3',

5'-AAGCTTAAGG-GTTCAC-CGAAA-GTTCAC-TCAGCTT-3',

5'-AAGCTTAAGG-GTTCAC-CGAAA-GTTCAC-TC-GCAT-AGCTT-3', or

5'-AAGCTTAAGG-GTTCAC-CGAAA-GTTCAC-TCGCAT-ATATT-AGCTT-3';

wherein said DNA segment is operatively linked to a promoter which is not normally subject to transcriptional activation by retinoic acid; wherein the DNA and the promoter are operatively linked so as to confer transcriptional activation activity on said promoter in the presence of retinoic acid.

8. A DNA construct according to claim 6 wherein the promoter is the delta-MTV promoter of mouse mammary tumor virus.

9. A DNA construct according to claim 7 wherein the promoter is the delta-MTV promoter of mouse mammary tumor virus.

10. A substantially pure DNA construct comprising the DNA construct of claim 9 linked operatively for transcription to a gene.

11. A vector for the expression of a protein of interest in a mammalian cell, said vector comprising the substantially pure DNA construct of claim 10, wherein said gene encodes the protein of interest.

12. A vector for the expression of a protein of interest in a mammalian cell, said vector comprising the substantially pure DNA construct of claim 10, wherein said gene encodes the protein of interest.

13. A vector according to claim 11 wherein the protein of interest is selected from luciferase, chloramphenicol acetyltransferase, and beta-galactosidase.

14. A vector according to claim 12 wherein the protein of interest is selected from luciferase, chloramphenicol acetyltransferase, and beta-galactosidase.

* * * * *

UNITED STATES PATENT AND TRADEMARK OFFICE
CERTIFICATE OF CORRECTION

PATENT NO. : 5,091,518

DATED : February 25, 1992

INVENTOR(S) : Henry M. Sucov and Ronald M. Evans

Page 1 of 2

It is certified that error appears in the above-indentified patent and that said Letters Patent is hereby corrected as shown below:

Column 1, lines 5-8, cancel the first paragraph in its entirety beginning with "The invention" to and including "in the invention."

Column 7, line 12, please delete "vector."

Column 9, claim 1, line 6, delete "substantially pure"; after "DNA" insert --segment comprising a β-retinoic acid response element operative to confer responsiveness to retinoic acid on the transcriptional activation of promoters in mammalian cells, said segment--;
    claim 2, line 12, after "DNA" insert --segment--;
    claim 3, line 14, after "DNA" insert --segment--;
    claim 4, line 19, after "DNA" insert --segment--;
    claim 5, line 24, after "DNA" insert --segment--;
    claim 6, line 29, delete "substantially pure";
    claim 6, line 30, after "DNA" insert --segment--;
    claim 6, line 30, after "claim 1" insert --; wherein said DNA segment is--;
    claim 6, line 32, after "acid;" insert --wherein said promoter is operatively linked to a gene for transcription of said gene; and--;
    claim 6, line 32, after "wherein" delete "the" and insert in its place --said--;
    claim 6, line 32, after "DNA" insert --segment--;
    claim 7, line 36, delete "substantially pure."

Column 10, claim 7, line 13, after "wherein" delete "the" and insert in its place --said--;
    claim 7, line 13, after "DNA" insert --segment--;

UNITED STATES PATENT AND TRADEMARK OFFICE
CERTIFICATE OF CORRECTION

PATENT NO. : 5,091,518
DATED : February 25, 1992
INVENTOR(S) : Henry M. Sucov and Ronald M. Evans It is certified that error appears in the above-indentified patent and that said Letters Patent is hereby corrected as shown below:

Column 10, claim 7, line 14, before "promoter" delete "the" and insert in its place --said--;
claim 10, line 23, delete "substantially pure";
claim 10, line 24, delete "linked";
claim 10, line 24, after "operatively" insert linked to a gene--;
claim 10, line 25, after "transcription" delete "to a gene" and insert --thereof.--;
claim 11, lines 27 and 28, delete "substantially pure";
claim 11, line 28, after "claim" delete "10" and insert --8--;
claim 12, lines 31 and 32, delete "substantially pure";
claim 13, line 36, after "acetyltransferase," delete "and" and insert --or--;
claim 14, line 39, after "acetyltransferase," delete "and" and insert --or--.

Signed and Sealed this

Fourteenth Day of December, 1993

Attest:

BRUCE LEHMAN

Attesting Officer

Commissioner of Patents and Trademarks